(12) United States Patent
Fayyaz et al.

(10) Patent No.: US 12,201,514 B2
(45) Date of Patent: Jan. 21, 2025

(54) SYSTEMS AND METHODS FOR INTRA-OCULAR LENS ADVANCEMENT

(71) Applicant: Alcon Inc., Fribourg (CH)

(72) Inventors: Asif Fayyaz, Fort Worth, TX (US); Sudarshan B. Singh, Euless, TX (US); Chris Belisle, Somerset, WI (US); Bill Hartsig, Hudson, WI (US); Sam Jang, Woodbury, MN (US)

(73) Assignee: ALCON INC., Fribourg (CH)

( * ) Notice: Subject to any disclaimer, the term of this patent is extended or adjusted under 35 U.S.C. 154(b) by 101 days.

(21) Appl. No.: 17/809,419

(22) Filed: Jun. 28, 2022

(65) Prior Publication Data

US 2022/0323206 A1    Oct. 13, 2022

Related U.S. Application Data

(63) Continuation of application No. 16/595,956, filed on Oct. 8, 2019, now Pat. No. 11,413,136, which is a continuation of application No. 15/626,291, filed on Jun. 19, 2017, now Pat. No. 10,470,875.

(60) Provisional application No. 62/354,010, filed on Jun. 23, 2016.

(51) Int. Cl.
  *A61F 2/16*  (2006.01)
  *A61F 9/00*  (2006.01)

(52) U.S. Cl.
  CPC .......... *A61F 2/1672* (2013.01); *A61F 2/1662* (2013.01); *A61F 9/0017* (2013.01)

(58) Field of Classification Search
  CPC ..... A61F 2/1672; A61F 2/1662; A61F 9/0017
  See application file for complete search history.

(56) References Cited

U.S. PATENT DOCUMENTS

2014/0257317 A1*  9/2014  Safabash ............... A61F 2/1662
                                                                  606/107

* cited by examiner

*Primary Examiner* — Phong Son H Dang

(57) ABSTRACT

An intraocular lens (IOL) insertion apparatus includes a handpiece body having a distal tip and a proximal section. The IOL insertion apparatus also includes a folding chamber located within the handpiece body, the folding chamber shaped to fold an IOL advancing through the folding chamber. The IOL insertion apparatus also includes an advancement system. The advancement system includes an advancement carriage movable between a first position and a second position within the handpiece body. The advancement carriage includes a spring system biasing the advancement carriage in a distal direction toward the second position and a dampening system to dampen motion of the advancement carriage. The advancement system further includes an elongated advancement plunger that includes a distal end to advance the IOL through the folding chamber and a proximal end connected to the advancement carriage.

11 Claims, 5 Drawing Sheets

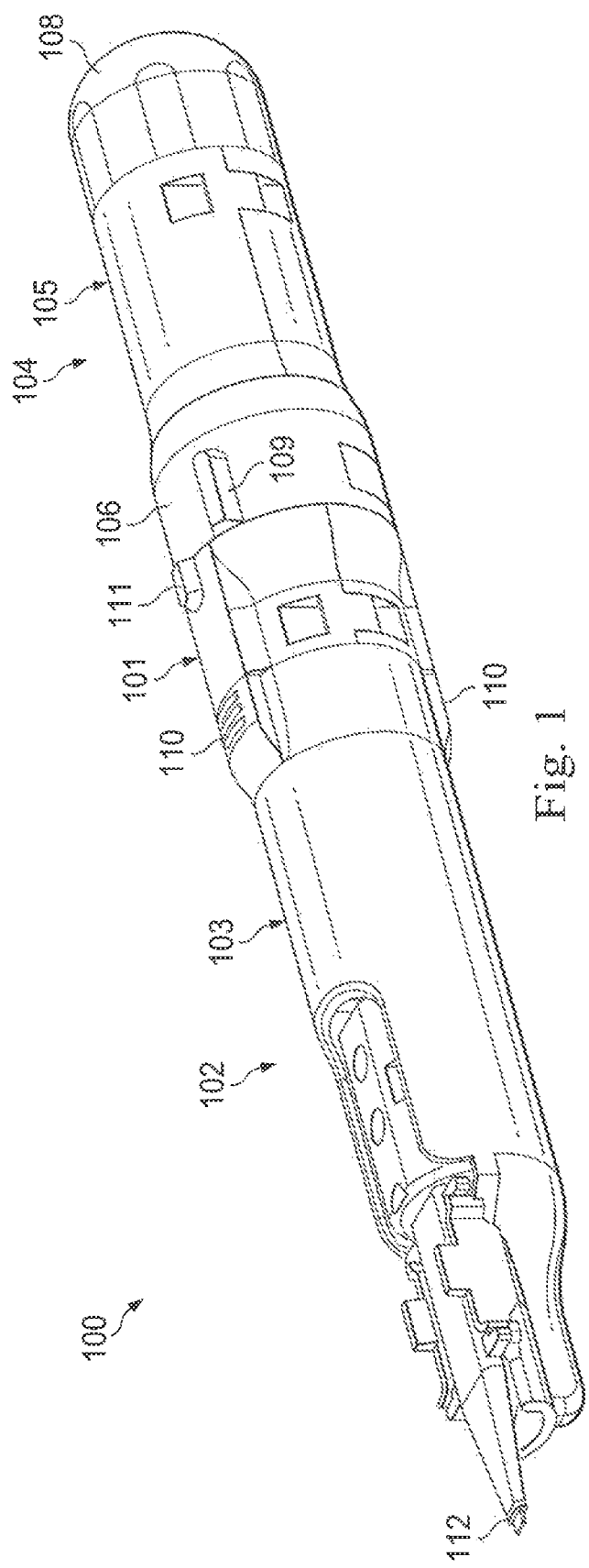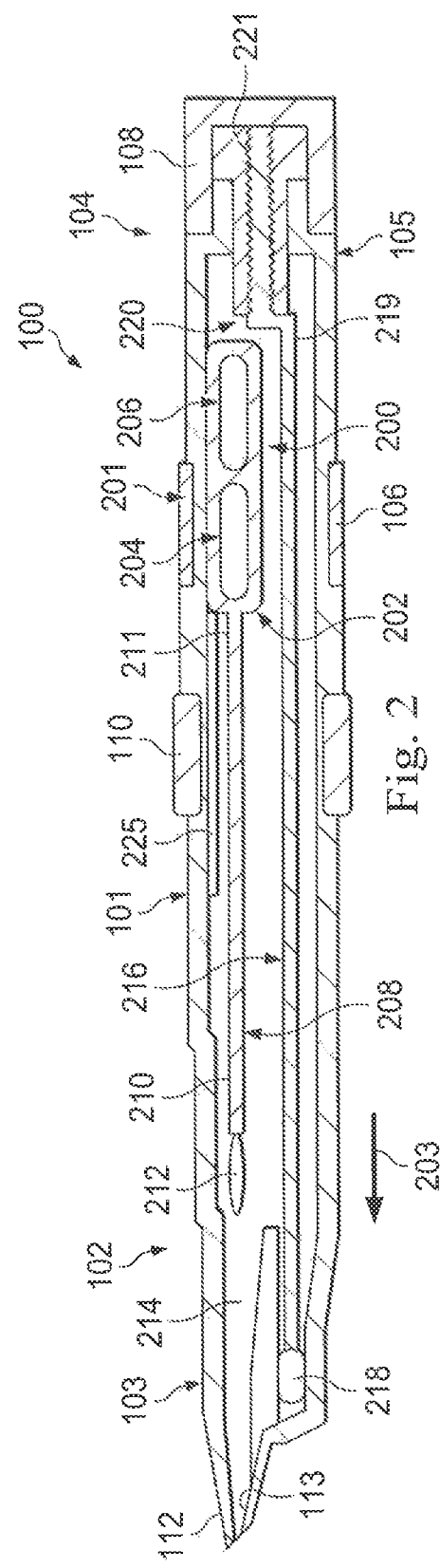

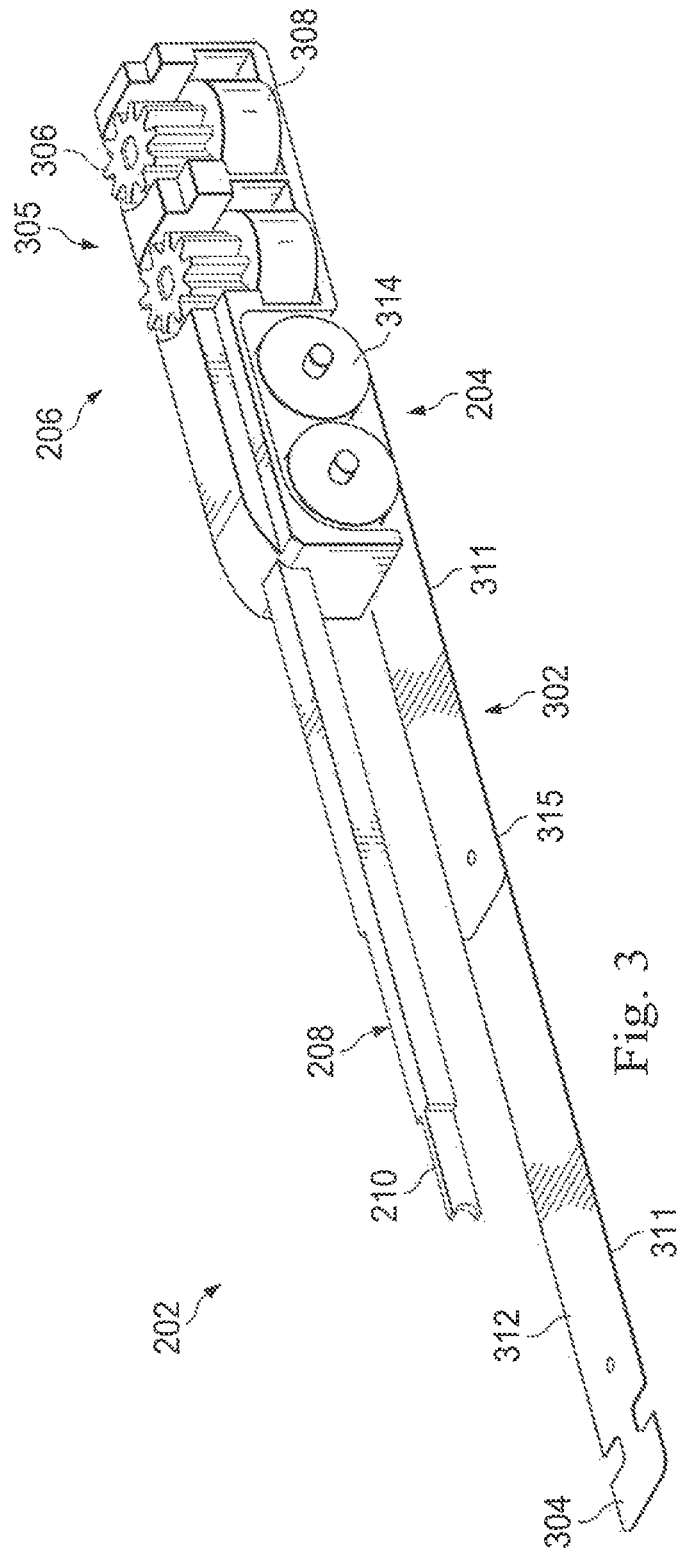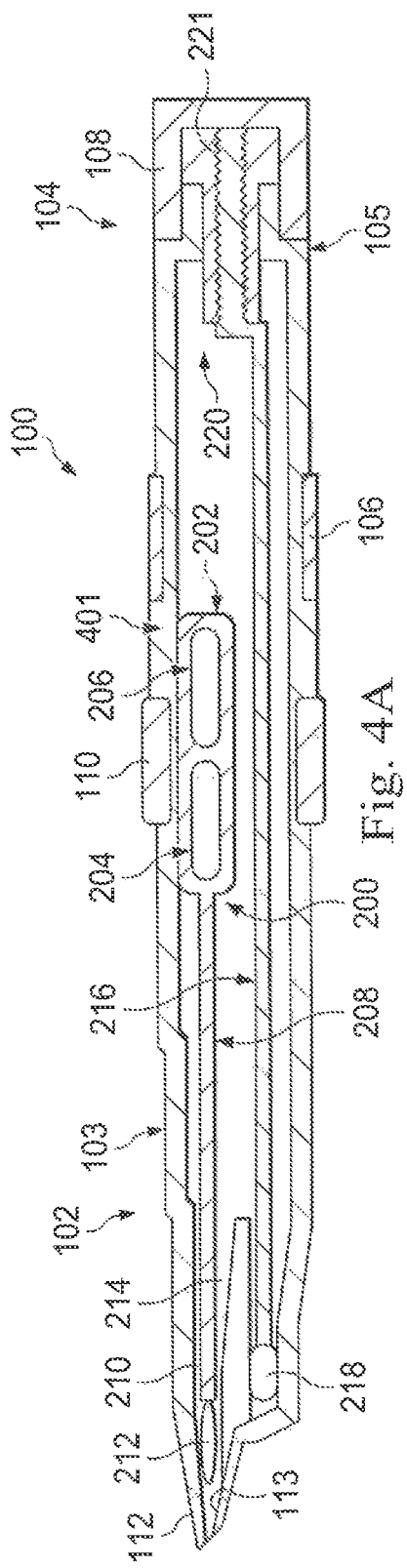

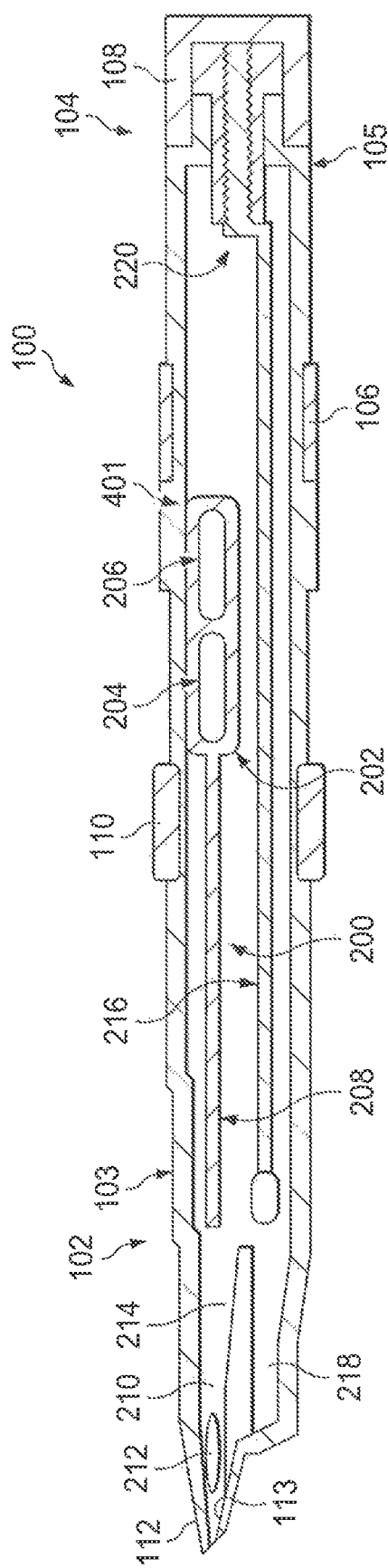
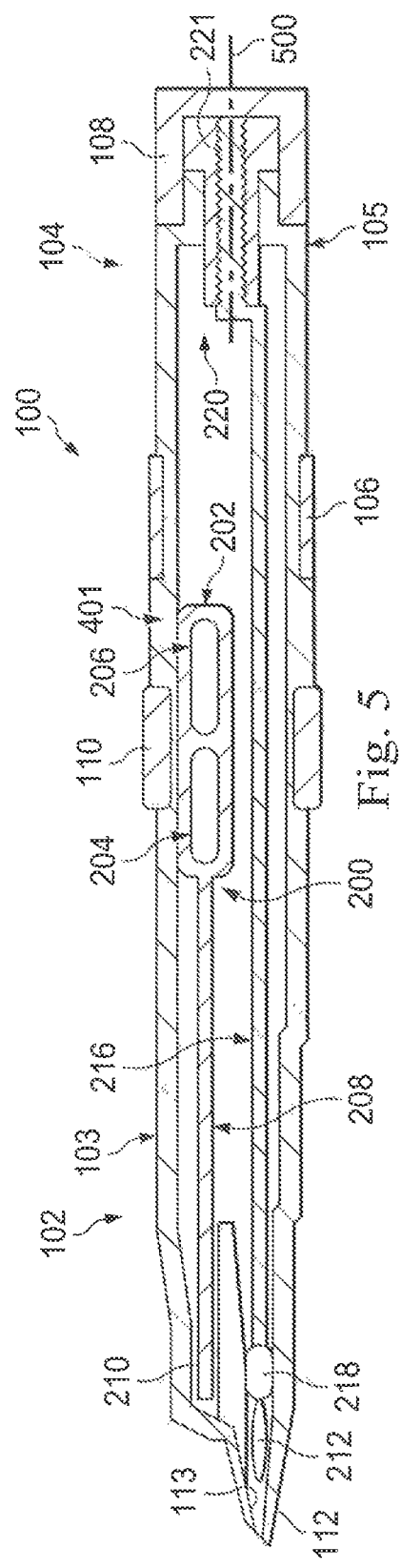
Fig. 4B
Fig. 5

SYSTEMS AND METHODS FOR INTRA-OCULAR LENS ADVANCEMENT

PRIORITY CLAIM

This Application is a continuation of U.S. Non-Provisional application Ser. No. 16/595,956, filed Oct. 8, 2019, which is a continuation of U.S. Non-Provisional application Ser. No. 15/626,291, filed Jun. 19, 2017, which claims the benefit of U.S. Provisional Application No. 62/354,010, filed Jun. 23, 2016, the entire contents of which are incorporated herein by reference.

TECHNICAL FIELD

The present disclosure is directed to methods and systems for performing ophthalmic surgical procedures, and more particularly, to methods and systems for advancing an intraocular lens for an ophthalmic surgical procedure.

BACKGROUND

The human eye, in simple terms, functions to provide vision by refracting light passing through a clear outer portion called the cornea and focusing the light by way of the lens onto the retina at the back of the eye. The quality of the visual image created by the focused light depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the natural lens and implantation of an artificial lens, typically termed an intraocular Lens (IOL).

Insertion of an IOL is typically performed using an IOL insertion tool. A conventional IOL insertion tool includes an IOL insertion cartridge that may fold and insert the IOL through a relatively small incision into the eye. For example, the IOL cartridge may include a folding chamber that has walls shaped cause the IOL to fold as desired as the IOL is moved through the chamber. Then, the folded IOL may be deployed into the patient's eye through the small incision. Typically, the operator of the IOL insertion tool manually pushes the IOL through the folding chamber by using a plunger that is engaged with the IOL. Various operators, however, may not apply appropriate force on the plunger as the plunger moves through the folding chamber. This can lead to undesirable folding results.

SUMMARY

An intraocular lens (IOL) insertion apparatus may include a handpiece body having a distal tip and a proximal section. The IOL insertion apparatus may also include a folding chamber located within the handpiece body. The folding chamber may be shaped to fold an IOL advancing through the folding chamber. The IOL insertion apparatus may also include an advancement system. The advancement system may include an advancement carriage movable between a first position and a second position within the handpiece body. The advancement carriage may include a spring system biasing the advancement carriage in a distal direction toward the second position and a dampening system to dampen motion of the advancement carriage. The advancement system may further include an elongated advancement plunger that includes a distal end to advance the IOL through the folding chamber and a proximal end connected to the advancement carriage.

A trigger mechanism may secure the advancement carriage in the first position and, upon actuation of the trigger mechanism, release the advancement carriage such that the spring system moves the advancement carriage in the distal direction toward the second position. The actuation mechanism may include a ring that, when rotated relative to the handpiece body into a specified rotational position, releases the advancement carriage. The handpiece body may include a distal section. The proximal section may be slidingly displaceable from and rotatable relative to the distal section. A deployment plunger may be selectively engageable with the IOL. The sliding displacement and rotation of the proximal section relative to the distal section may align the deployment plunger with the IOL. The deployment plunger may include a compressible distal tip operative to the IOL. The advancement carriage may prevent sliding and rotating of the proximal section relative to the distal section until the advancement carriage has advanced in a distal direction from the first position. A threaded mechanism may be cooperatively engaged with the deployment plunger. Rotation of the threaded mechanism relative to the deployment plunger may distally advance the deployment plunger. The spring system may include a plurality of constant force springs. The dampening system may include a track extending a length of the handpiece body and one or more gears that engage the track. The distal end of the advancement plunger may include a rigid material.

An intraocular lens (IOL) insertion apparatus may include a handpiece body having a proximal section and a distal section; an advancement body; an advancement plunger; a deployment plunger; a deployment mechanism; and a trigger mechanism. The distal section may form a passage extending through at least a portion of the distal section and configured to dispense an intraocular lens. The distal section may be rotatable relative to the proximal section between a first rotational position and a second rotational position. The advancement carriage may include a spring to bias the advancement carriage in a first direction disposed within the handpiece body and longitudinally moveable therein. The advancement plunger may be connected to a proximal end of the advancement carriage. The deployment plunger may be angularly offset from the advancement plunger about a longitudinal axis of the handpiece body. The deployment mechanism may be operably connected to the deployment plunger, and the deployment mechanism may be actuatable to advance the deployment plunger. The trigger mechanism may be moveable between a lock position in which the advancement carriage is prevented from moving within the handpiece body and a release position in which the advancement carriage is released and permitted to move within the handpiece body. When distal section is in the first rotational position, the advancement plunger may align with the passage formed in the distal section, and, when the distal section is in the second rotational position, the deployment plunger may align with the passage formed in the distal section.

The advancement carriage may also include a dampening system to dampen motion of the advancement carriage in the first direction. The dampening system may include a track extending a length of the handpiece body, a gear that engages the track, and a viscous fluid. Rotational motion of the gear may cause the viscous fluid to produce a resistive force that limits the rotational motion of the gear. A guiderail may be disposed along an interior of the handpiece body to guide the advancement carriage from a first position to second position after being released by the trigger mechanism. A lock mechanism may be operative to prevent rotation of the proximal section relative to the distal section until the advancement carriage is in the second position. The deployment mechanism may include a rotational mechanism rotatable by a user. The rotational mechanism may include a threaded mechanism cooperatively engageable with the deployment plunger and arranged to displace the deployment plunger in a distal direction in response to rotation of the threaded mechanism.

A method includes positioning a distal end of an intraocular lens (IOL) insertion apparatus handpiece at a surgical site and triggering a trigger mechanism that releases an advancement carriage. The advancement carriage has an advancement plunger extending from a distal end of the advancement carriage. The advancement carriage is spring biased in a distal direction such that, when released, the advancement carriage moves a distal tip of the advancement plunger through a folding chamber to fold an IOL engaged with the distal tip. The method further includes rotating a proximal section of the handpiece with respect to a distal section of the handpiece to align a deployment plunger with the folded IOL.

A deployment mechanism positioned at a proximal end of the handpiece may be rotated to move the deployment plunger distally to inject the folded IOL into an eye of a patient. The proximal section may be pulled away from the distal section before rotating the proximal section. The proximal section may be pushed towards the distal section after rotating the proximal section.

BRIEF DESCRIPTION OF THE DRAWINGS

The accompanying drawings illustrate embodiments of the devices and methods disclosed herein and together with the description, serve to explain the principles of the present disclosure.

FIG. 1 is a diagram showing an illustrative intraocular lens insertion apparatus that provides automated advancement of an intraocular lens.

FIG. 2 is a diagram showing a cross-sectional view of a portion of the intraocular lens insertion apparatus of FIG. 1 that provides automated advancement of an intra-ocular lens.

FIG. 3 is a perspective view of an illustrative advancement carriage for use in the intraocular lens insertion apparatus of FIG. 1.

FIG. 4A is a diagram showing a cross-sectional view of an intraocular lens insertion apparatus with the advancement carriage in a forward position.

FIG. 4B is a diagram showing a cross-sectional view of the intraocular lens apparatus with the proximal section longitudinally displaced from the distal section.

FIG. 5 is a diagram showing a cross-sectional view of an intraocular lens insertion apparatus with a deployment plunger engaged with the intraocular lens.

DETAILED DESCRIPTION

Figure 6:
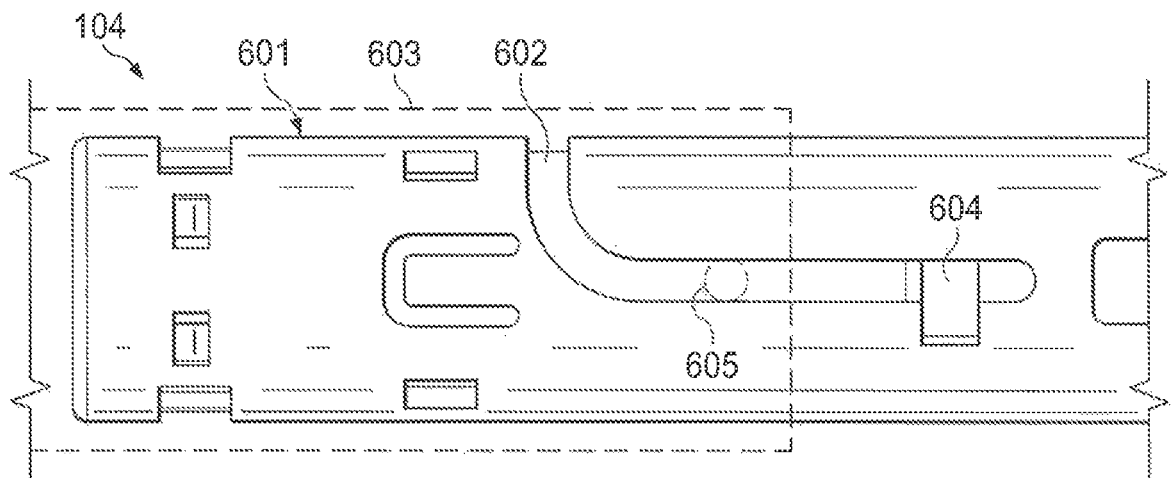
FIG. 6 is a side-view of a guidance track for a proximal section of an intraocular lens insertion apparatus.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

As described above, various operators of an IOL insertion tool may not apply appropriate force on the plunger as the plunger moves through the folding chamber. For example, some operators may apply too much force while other operators apply too little force. This can lead to undesirable folding results.

According to principles described herein, an IOL insertion apparatus provides automated advancement of the IOL through the folding chamber. In some examples, actual deployment of the IOL into the patient's eye may be manually controlled. Because of the automated advancement of the IOL, the force applied on the plunger may be consistent and predictable, irrespective of the operator. This may provide a higher percentage of properly folded lenses than can be obtained with conventional systems. Furthermore, the automated advancement of the IOL through the folding chamber may be self-contained within the IOL insertion tool and not rely on any external powering mechanism.

In some examples of principles described herein, an IOL insertion apparatus includes a handpiece body that includes a folding chamber. An advancement carriage may be releasably secured at a proximal position within the handpiece body. Attached to the advancement carriage may be an advancement plunger. The advancement plunger may have a rigid distal end configured to engage the IOL and push the IOL through the folding chamber. In some implementations, the advancement carriage may be spring-biased in the distal direction such that when the advancement carriage is released, it moves in a distal direction, thereby causing the advancement plunger to push the IOL through the folding chamber. In some examples, the advancement carriage also includes a dampening system to dampen the distal motion of the advancement carriage after being released. The IOL insertion tool with automated advancement of the IOL will be described in further detail below.

FIG. 1 shows an illustrative IOL insertion apparatus 100 that provides automated advancement of an IOL. According to the present example, the IOL insertion apparatus 100 includes a handpiece body 101 having a distal section 102 with a distal tip 112 and having a proximal section 104. The distal section 102 includes a distal body 103 and the proximal section 104 includes a proximal body 105. The IOL insertion apparatus 100 also includes a set of release tabs 110 and includes a trigger mechanism 106. The IOL insertion apparatus 100 also includes a deployment actuator 108.

The handpiece body 101 is arranged to be gripped by an operator such as a surgeon. Thus, the handpiece body 101 may be ergonomically shaped for gripping by hand. In some examples, the IOL insertion apparatus may be a single-use device that may be discarded after the IOL within the IOL insertion apparatus has been inserted into the patient's eye.

The trigger mechanism 106 may be used to initiate movement of the IOL through a folding chamber 214 (shown in FIG. 2) to fold the IOL. In this particular example, the trigger mechanism 106 is a release ring. An operator may trigger the folding process by, for example, rotating the release ring 106 to a specific rotational position. The specific rotational position may be, for example, when protrusion 109 of the release ring 106 is aligned with protrusion 111 of the handpiece body 101.

The release tabs 110 may be used to release the proximal section 104 from the distal section 102. As will be described in further detail below, the proximal section 104 may be moved a predefined distance away from the distal section 102, rotated approximately 180 degrees, and then moved back towards the distal section 102. This motion prepares the IOL insertion apparatus 100 for the deployment process. The deployment process involves moving the IOL outside of the distal tip 112 of the IOL insertion apparatus 100 and into the patient's eye.

The deployment actuator 108 may be used to perform the deployment process to introduce the IOL to the patient's eye. In the present example, the deployment actuator 108 is a rotatable knob positioned at the proximal end of the handpiece body 101. An operator may rotate the deployment actuator 108 to move the folded IOL out of the IOL insertion apparatus 100 and into the patient's eye.

FIG. 2 is a diagram showing a cross-sectional view of the IOL insertion apparatus 100 that provides automated advancement of an IOL. The cross-sectional view illustrates an advancement system 200 that includes an advancement carriage 202 and an advancement plunger 208. The cross-sectional view also illustrates an IOL 212, the folding chamber 214, a threaded deployment mechanism 220, and the deployment plunger 216.

According to the present example, the advancement carriage 202 is secured at a proximal position 201 within the handpiece body 101. The advancement carriage 202 includes a spring system 204 and a dampening system 206. The spring system 204 may bias the advancement carriage 202 towards a distal end of the IOL insertion apparatus 100. The advancement carriage 202 may remain at the proximal position 201 until the advancement carriage 202 is released from the proximal position 201 when an operator actuates the trigger mechanism 106. After being released from the proximal position 201, the advancement carriage 202 moves in a distal direction as indicated by arrow 203. The rate at which the advancement carriage 202 moves distally is controlled by the dampening system 206 and the spring system 204.

Movement in the distal direction of the advancement carriage 202 causes corresponding movement in the distal direction of the advancement plunger 208. The advancement plunger 208 is an elongated structure that has a proximal end 211 secured to the advancement carriage 202. The advancement plunger 208 has a distal end or tip 210 that is configured to engage the IOL 212. The advancement carriage 202 may be supported and guided in its movement by a number of support and guidance structures. For example, in some implementations, the interior of the body may include one or more guiderails 414 formed along an interior surface of the handpiece body 101. The guiderails 414 guide the advancement carriage 202 from the proximal position 201 to a distal position after the advancement carriage 202 is released by the trigger mechanism 106. The advancement carriage 202 may engage the guiderail 415 such that the advancement carriage 202 follows the guiderail as the advancement carriage 202 is displaced within the handpiece body 101 (not shown).

Figure 8:
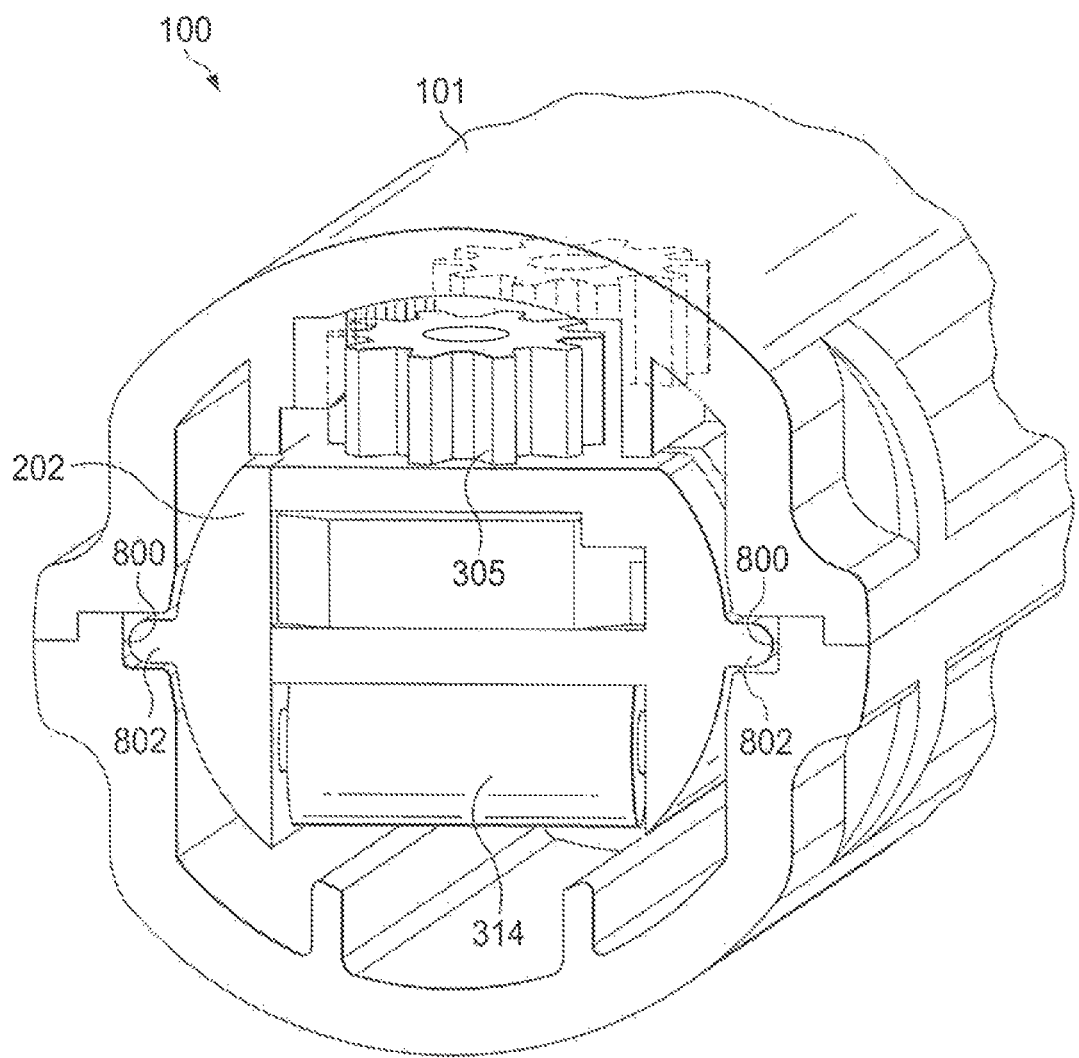
FIG. 8 is a cross-sectional view of the example intraocular lens insertion apparatus of FIG. 1 showing an advancement carriage with tabs received into grooves formed within a handpiece body of the IOL insertion apparatus.

FIG. 8 shows an example of guiderails in the form of grooves 800 formed into the handpiece body 101. In other implementations, one or more of the grooves 800 may be defined by or formed in another component disposed within the IOL insertion handpiece 100. In the illustrated example, the advancement carriage 202 includes tabs 802 that are received into the grooves 800. In some instances, the tabs 802 extend along only a portion of a length of the advancement carriage 202. In other implementations, the tabs 802 may extend along an entire length of the advancement carriage 202. Still further, although FIG. 8 shows only two tabs 802, in other implementations, the advancement carriage 202 may include more than two tabs 802 or less than two tabs 802. The interaction between the grooves 800 and the tabs 802 keeps the advancement carriage 202 properly aligned and positioned within the IOL insertion device 100 as the advancement carriage 202 is advanced, as shown, for example, in FIG. 8. The tabs 316 cooperate with the grooves to control an orientation and advancement of the advancement carriage 202 as the advancement carriage 202 advances through the handpiece body 101.

In some implementations, the tip 210 of the advancement plunger 208 may be substantially rigid. That is, a hardness of the tip 210 may be much larger than a hardness of the IOL 212 or tip 218, described in more detail below. Thus, the rigid tip 210 may more efficiently engage the IOL 212 to push the IOL 212 through the folding chamber 214. After the IOL 212 passes through the folding chamber 214, the IOL 212 approaches the distal tip 112 of the IOL insertion apparatus 100. The distal tip 112 of the IOL insertion apparatus 100 includes a narrowing region 113 near a distal end of the distal tip 112 that is in fluid communication with the folding chamber 212. The narrowing region 113 defines a narrowing region through which the IOL 212 passes as the IOL 212 is advanced through the IOL insertion apparatus 100.

Because the rigid tip 210 of the advancement plunger 208 is not compressible, the tip 210 is not able to extend into the narrowing region 113 of the distal tip 112.

The deployment plunger 216 is an elongated structure that has a proximal end 219 having a threaded portion 221. The threaded portion 221 may be engaged with a threaded deployment mechanism 220. FIG. 2 illustrates the advancement plunger 208 positioned to engage the IOL 212. However, as will be described in further detail below, the IOL insertion apparatus 100 can be configured such that the deployment plunger 216 is positioned to engage the IOL 212. When the deployment plunger 216 is positioned to engage the IOL 212, rotation of the deployment actuator 108 rotates the threaded deployment mechanism 220. Rotation of the threaded deployment mechanism 220 moves the deployment plunger 216 in a distal direction to push the IOL 212 out of the distal tip 112.

The deployment plunger 216 includes the tip 218. In some implementations, the tip 218 may be made of a compressible material. Thus, when the deployment plunger 216 engages the IOL 212, the tip 218 may be compressed and made to conform to the passage formed by the distal tip 112, including the narrowing region 113 so as to move the IOL 212 out of the IOL insertion apparatus 100 and into the patient's eye.

FIG. 3 is a perspective view of the advancement carriage 202 for use in an IOL insertion apparatus (e.g., the IOL insertion apparatus 100 shown in FIG. 1). As described above, the advancement carriage 202 includes a spring system 204 and dampening system 206. In the present example, the spring system 204 includes a number of constant force springs 302. A constant force spring is one in which the force applied by the spring remains constant despite the position of the spring. In other words, a constant force spring does not follow Hooke's law.

In the present example, the constant force springs 302 include a coil 314, an unrolled portion 315, a pickup portion 312, and a mounting tab 304. In one example, the coils 314 include rolled-up, elongated metal sheets 311. The sheets 311 may be biased to the rolled-up position. Thus, when the sheets 311 are extended or unrolled as represented by the unrolled portion 315, the sheets 311 will revert back to a rolled-up state absent any structure or force preventing the sheets 311 from doing so. A distal end of one of the constant force springs 302 may include the mounting tab 304, which is configured to be secured to an interior of the handpiece body 101. In some examples, a distal section of the sheets 311 may include a pickup portion 312. The pickup portion 312 does not have spring-like properties. The pickup portion 312 provides for ease of assembly and maintaining a substantially flat profile within a space between the advancement carriage 202 and a location to which the mounting tab 304 is secured. When the advancement carriage 202 is released, unrolled portions of the springs 302 roll-up to form part of the coils 314, providing a constant force to the advancement carriage 202, and thereby advancing the advancement carriage 202 in the distal direction. While the present example illustrates only two constant force springs 302, other embodiments may include only one constant force spring or more than two constant force springs.

The dampening system 206 helps control the distal movement of the advancement carriage 202 after the advancement carriage 202 has been released. In other words, the dampening system 206 prevents the advancement carriage from moving too fast once released by the trigger mechanism (e.g., advancement trigger 106 as shown in FIG. 1). In the present example, the dampening system 206 includes a number of rotary dampers 305. The rotary dampers 305 may include an injection molded body 308 and a pinion 306. The body 308 may include a viscous fluid, a rotor (not shown), and a stator (not shown). The rotary damper 305 provides fluid damping through the shearing force of the fluid resistance between the surfaces of the rotor and stator. The pinion 306 includes a number of teeth that are configured to engage a track that extends along an inner surface of the handpiece body 101. While the present example illustrates two rotary dampers 305, other embodiments may include a single rotary damper or more than two rotary dampers.

FIG. 4A is a diagram showing a cross-sectional view of the IOL insertion apparatus 100 with the advancement carriage 202 in a distal position 401. As described above, the trigger mechanism 106 may be used to release the advancement carriage 202 from its proximal position (e.g., proximal position 201 shown in FIG. 2). After being released, the combination of the spring system 204 and the dampening system 206 of the advancement carriage 202 moves the advancement carriage 202 forward at a controlled rate. The controlled rate is defined in part by the dampening system 206. Forward motion (i.e., movement towards the distal tip 112) of the advancement carriage 202 causes the advancement plunger 208 to move the IOL 212 through the folding chamber 214 and into a position within the narrowing region 113 of the distal tip 112. Ultimately, the advancement carriage 202 stops in the distal position 401. In some examples, the advancement carriage 202 may be physically prevented from moving any further in the distal direction after the advancement carriage 202 reaches the distal position 401.

FIG. 4B is a diagram showing a cross-sectional view of the IOL lens insertion apparatus 100 with the proximal section 104 longitudinally displaced from the distal section 102. After the advancement carriage 202 has been moved to the distal position 401, an operator uses the release tabs 110 to release the proximal section 104 from the distal section 102. The proximal section 104 is then movable in a direction away from the distal section 102. In some examples, as will be described in further detail below, a guidance track may be used to guide the proximal section 104 as it is moved away from the distal section 102.

FIG. 5 is a diagram showing a cross-sectional view of the IOL insertion apparatus 100 with the deployment plunger 216 engaged with the IOL 212. In other words, the distal section 102 has been rotated about longitudinal axis 500 of the IOL insertion apparatus relative to the proximal section 104 such that instead of the advancement plunger 208 being aligned with the IOL 212, the deployment plunger 216 is aligned with the IOL. In some implementations, the distal section 102 may be rotated 180 degrees about the longitudinal axis 500 relative to the proximal section 104. In some examples, the distal section 102 is released from the proximal section 104 through use of the release tabs 110. In some examples, the release tabs 110 are physically prevented from releasing the proximal section 104 from the distal section 102 until the advancement carriage 202 has moved into the distal position 401. This helps to ensure that the IOL 212 is moved into the appropriate position before the advancement plunger 208 is removed from engagement with the IOL 212 and the deployment plunger 216 is engaged with the IOL 212.

In one example, an operator of the IOL insertion apparatus 100 moves the proximal section 104 away from the distal section 102 after pressing the release tabs 110. The proximal section 104 may be slidingly engaged with the distal section 102 such that as the operator moves the proximal section 104 from the distal section 102, a region of the proximal body 105 slides along a region of the distal body 103. The operator moves the proximal section 104 at least a predefined distance away from the distal section 102 such that the advancement plunger 208 clears the folding chamber 214, as shown in FIG. 4B. The operator may then rotate the proximal section 104 relative to the distal section 102 such that the deployment plunger 216 is aligned with the IOL 212. In one example, the proximal section 104 is rotated about 180 degrees relative to the distal section 102. The operator may then move the proximal section 104 towards the distal section 102 to a point where the proximal section 104 reconnects with the distal section 102. As a result, the tip 218 of the deployment plunger 216 passes through the folding chamber and engages the IOL 212 positioned within narrowing region 113.

To aid the operator with moving and rotating the proximal section 104 with respect to the distal section 102, the proximal body 105 and the distal body 103 may include guidance features. For example, the distal body 103 may include a track while the proximal body 105 may include a protrusion that fits within the track. Conversely, the proximal body 105 may include a track while the distal body 103 may include a protrusion.

After the proximal section 104 has been rotated relative to the distal section 102 and the deployment plunger 216 has been engaged with or been brought into close proximity to the IOL 212, the operator may use the deployment actuator 108 to move the deployment plunger 216 forward. Specifically, rotation of the deployment actuator 108 causes corresponding rotation of the threaded deployment mechanism 220. As described above, the threaded deployment mechanism 220 includes threads that engage with threads of the threaded portion 221 of the deployment plunger 216. Thus, rotation of the threaded deployment mechanism 220 moves the threaded portion 221 in a linear motion, and correspondingly, causes the deployment plunger 216 to move distally in a linear motion. As the deployment plunger 216 is moved distally, the IOL 212 also is moved distally and, ultimately, out of the distal tip 112 of the IOL insertion apparatus 100 and into a patient's eye. As described above, the tip 218 of the deployment plunger 216 may be made of a compressible material so that the tip 218 conforms to the passage defined by the narrowing region 113 of the distal tip 112 as the tip 218 is advanced therethrough. Consequently, the IOL 212 is made to advance through and out of the IOL insertion apparatus 100.

FIG. 6 illustrates a side-view of an example guidance track 602 that may be formed in or otherwise incorporated into the proximal section 104 of the IOL insertion apparatus 100. As shown in FIG. 6, a distal end 601 of the proximal body 105 includes the guidance track 602. The distal end 601 may be generally covered by a proximal end of the distal body 103 when the IOL insertion apparatus 100 is fully assembled. Thus, the guidance track 602 is generally not visible to an operator of the assembled IOL insertion apparatus 100. The distal body 603 may include a pin 605 that fits within the guidance track 602. The guidance track 602 guides the pin 605 and, thus, the proximal section 104 as it is moved and rotated relative to the distal section 102. In some instances, the guidance track 602 may be substantially U-shaped and positioned along the proximal body 105 in a manner such that the parallel portions of the U-shaped guidance track 602 extend longitudinally along the IOL insertion apparatus 100.

As shown in FIG. 6, the proximal end of the distal body 103 may have a corresponding guide pin 605 that fits within the guidance track 602. At its original position, the guide pin 605 may reside within location 604. In some examples, the guide pin 605 may be physically prevented from moving from location 604 into the guidance track 602 until the advancement carriage 202 reaches the distal position 401.

Figure 7:
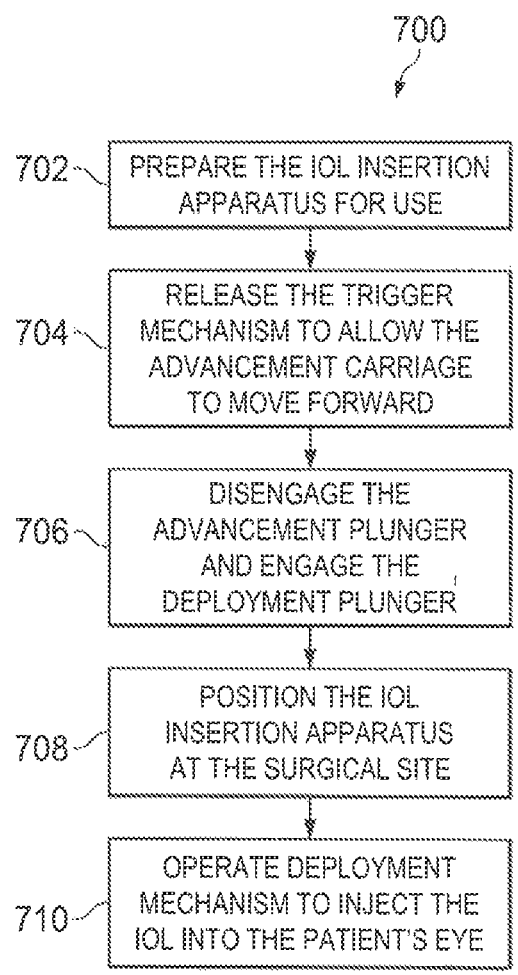
FIG. 7 is a flowchart showing an illustrative method for using an intraocular lens insertion apparatus that provides automated advancement of the intraocular lens.

FIG. 7 is a flowchart showing an illustrative method for using an IOL insertion apparatus that provides automated advancement of the IOL. According to the present example, the method 700 includes a step 702 for preparing the IOL insertion apparatus for use. Preparing the IOL for use may involve removing an IOL lockout mechanism (not shown) and injecting a lubricant into the handpiece body.

The IOL insertion apparatus may come packaged with the IOL placed proximally outside the folding chamber in an unfolded state. The IOL itself may also be secured in place through an IOL lockout mechanism. The IOL lockout mechanism may be a mechanical piece attached to the exterior of the handpiece body (such as the handpiece body 101 shown in FIG. 1). When attached to the handpiece body, the IOL lockout mechanism mechanically secures the IOL in place to protect it from unwanted movement during shipping. The IOL lockout mechanism may also mechanically block forward motion of the advancement carriage to avoid premature triggering of the advancement process.

After the IOL lockout mechanism has been removed, the operator may inject a lubricant into the handpiece body. Such lubricant may fill a space around the IOL in the folding chamber to provide lubrication for the IOL as it passes through the folding chamber. In one example, the lubricant may be an Ophthalmic Visio-surgical Device (OVD) fluid.

The method 700 further includes a step 704 for releasing the trigger mechanism to allow the advancement carriage to move forward. In some instances, the operator may press a button, rotate a ring, or trigger or actuate a mechanism that mechanically releases the advancement carriage. Because the advancement carriage is spring biased in the distal direction, the advancement carriage moves from a first, proximal position to a second, distal position within the handpiece body. Because the advancement carriage is attached to an advancement plunger, movement in the distal direction of the advancement carriage causes movement in the distal direction of the advancement plunger, which moves the IOL out of its original placement and through the folding chamber. Passage of the IOL through the folding chamber causes the IOL to be folded as desired before the IOL is inserted into the patient's eye.

The method 700 further includes a step 706 for disengaging the advancement plunger from the IOL and engaging the deployment plunger with the IOL. This may be done, for example, by pulling, rotating, and pushing the proximal section of the IOL insertion apparatus relative to the distal section of the IOL insertion apparatus as described above.

The method 700 further includes a step 708 for positioning the IOL insertion apparatus at a surgical site. In some examples, a small incision is made in the patient's eye at the surgical site. In some examples, the incision may be less than 2 millimeters. Placement of the IOL insertion apparatus involves placing a distal tip of the IOL insertion apparatus at the incision such that when the IOL is moved out of the distal tip, the IOL is passed through the incision.

The method 700 further includes a step 710 for operating the deployment actuator to inject the IOL into the patient's eye. As described above, the deployment actuator may be a rotatable knob positioned at the proximal end of the IOL insertion apparatus. Rotation of the deployment actuator causes rotation of the threaded deployment mechanism. Rotation of the threaded deployment mechanism causes movement of the deployment plunger in the distal direction. Movement in the distal direction of the deployment plunger moves the IOL out of the distal tip of the IOL insertion apparatus, through the incision, and into the patient's eye.

Use of methods and systems described herein provides a number of benefits and advantages. For example, because advancement of the IOL is automated rather than relying on varying human operators, there is less risk that the IOL will be advanced improperly. Furthermore, advancement of the IOL as described herein does not rely on any external power or connection. Instead, automated advancement of the IOL is accomplished mechanically through the spring and dampening systems described above. Thus, the IOL insertion apparatus is a self-contained device that is able to operate without being connected to any external machine.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An intraocular lens (IOL) insertion apparatus, comprising:
   a handpiece body having a proximal end and a distal end, and comprising:
      a folding chamber configured to fold an IOL, and
      a nozzle coupled to the folding chamber and comprising a distal tip having an opening;
   an advancement system, comprising:
      an advancement carriage moveable between a first position and a second position within the handpiece body,
      a spring system biasing the advancement carriage in a distal direction towards the second position, and
      a dampening system configured to dampen motion of the advancement carriage; and
   a first plunger having a proximal end coupled to the advancement carriage such that distal motion of the advancement carriage causes a corresponding distal motion of the first plunger and a distal end configured to advance the IOL through the handpiece body;
   wherein the IOL insertion apparatus is adapted to be changed from a first configuration for operation of the advancement system to a second configuration for ejection of the IOL from the opening of the nozzle.

2. The IOL insertion apparatus of claim 1, further comprising a second plunger configured to eject the IOL when the IOL insertion apparatus is in the second configuration.

3. The IOL insertion apparatus of claim 2, wherein the second plunger comprises a compressible distal tip.

4. The IOL insertion apparatus of claim 2, further comprising a threaded mechanism cooperatively engaged with the second plunger, wherein rotation of the threaded mechanism distally advances the second plunger.

5. The IOL insertion apparatus of claim 1, wherein the spring system comprises a constant force spring.

6. The IOL insertion apparatus of claim 5, wherein the constant force spring comprises a coil, an unrolled portion, and a mounting tab.

7. The IOL insertion apparatus of claim 1, wherein the dampening system comprises a track extending a length of the handpiece body and one or more gears that engage the track.

8. The IOL insertion apparatus of claim 7, wherein the one or more gears are in fluid communication with a viscous fluid for providing fluid dampening.

9. The IOL insertion apparatus of claim 1, wherein the distal end of the first plunger comprises a rigid material.

10. The IOL insertion apparatus of claim 1, further comprising a guiderail disposed along an interior of the handpiece body to guide the advancement carriage from the first position to the second position.

11. The IOL insertion apparatus of claim 1, wherein the coupling of the proximal end of the first plunger to the advancement carriage comprises a direct physical coupling.

* * * * *